(12) United States Patent
Dubnack

(10) Patent No.: US 6,347,244 B1
(45) Date of Patent: Feb. 12, 2002

(54) PROCESS AND ARRANGEMENT FOR TARGETED APPLICATION OF A THERAPY BEAM, PARTICULARLY FOR THE TREATMENT OF DISEASED AREAS IN THE EYE

(75) Inventor: Steffen Dubnack, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/394,535

(22) Filed: Sep. 10, 1999

(30) Foreign Application Priority Data

Apr. 1, 1999 (DE) .......................... 199 14 914

(51) Int. Cl.$^7$ ............................... A61B 6/00
(52) U.S. Cl. ..................... 600/476; 606/12; 606/10
(58) Field of Search ................... 606/3–5, 10, 11, 606/13; 600/431, 476

(56) References Cited

U.S. PATENT DOCUMENTS

| 5,350,374 A | * | 9/1994 | Smith .......................... 606/5 |
| 5,423,801 A | * | 6/1995 | Marshall et al. ............... 606/5 |
| 5,514,127 A | * | 5/1996 | Shanks ......................... 606/10 |
| 5,624,436 A | * | 4/1997 | Nakamura et al. ............ 606/12 |
| 5,624,437 A | * | 4/1997 | Freeman et al. ............... 606/12 |
| 6,019,755 A | * | 2/2000 | Steinert ......................... 606/5 |

* cited by examiner

Primary Examiner—Marvin M. Lateef
Assistant Examiner—Shawna J Shaw
(74) Attorney, Agent, or Firm—Reed Smith LLP

(57) ABSTRACT

The invention is directed to a process for the targeted application of therapy radiation in the treatment of diseased areas in the eye by means of a therapy beam which is directed into the eye through an applicator. In order to determine the parameters characterizing the diseased area, an image of the fundus of the eye to be treated is produced. The parameters characterizing the shape and/or size of the area to be irradiated and controlling variables are derived from this fundus image and are further processed by a computer. A control device is controlled by means of these parameters and controlling variables and adjusts or displaces an actuating arrangement corresponding to the shape and/or size of the area to be irradiated, which actuating arrangement changes the shape and/or size of the cross section of the therapy laser beam or changes the direction of the therapy laser beam in a plurality of coordinates and is arranged in the beam path of the therapy beam.

18 Claims, 3 Drawing Sheets

PROCESS AND ARRANGEMENT FOR TARGETED APPLICATION OF A THERAPY BEAM, PARTICULARLY FOR THE TREATMENT OF DISEASED AREAS IN THE EYE

BACKGROUND OF THE INVENTION a) Field of the Invention

The invention is directed to a process and an arrangement for targeted application of a therapy beam, especially for irradiation of diseased areas in the fundus oculi of the eye (retina, choroid or sciera), in order to implement an effective radiation therapy and to protect healthy tissue as far as possible.

b) Description of the Related Art

In ophthalmology, besides other therapy systems, lasers are also used for the treatment of diseased areas in the retina and other diseased areas in the eye. In this respect, it is frequently necessary to adapt the cross-sectional shape of the treatment laser beam to the peculiarities of the irradiated region or to the shape and dimensions of the affected area. It is known in the art to enlarge or reduce a laser beam utilized in ophthalmological therapy.

For example, it is known from DE 38 23 136 C2, which describes an optical system for a fundus camera for photographing the retina by scanning with a laser beam, to change the scanning spot in the illumination beam path by means of a beam expansion system. A zoom system is provided, for example, as a beam expansion system by means of which a continuous enlargement or reduction of the beam cross section can be carried out. Other possibilities for enlarging or reducing the beam cross section consist in the arrangement of diaphragms or lenses of different diameter in the beam path. However, it is not possible to change the cross-sectional shape of the therapy beam with the means mentioned above; only the size of the cross section is changed.

In a device for generating a laser beam spot of adjustable size in the human eye according to WO 87/01819, the laser beam cross section is adapted to the diseased region of the eye to be treated in that the laser beam rotates on paths of different radii. In order to generate this laser beam spot, for example, a rotating, tilted glass plate or nutating optical element or two mirrors which can be tilted in a controlled manner are provided in the therapy beam path. In this device, it is also impossible to adapt the cross-sectional shape of the laser beam to the shape of the irradiated area in the eye.

Further, U.S. Pat. No. 5,461,212 likewise discloses diaphragms, for example, in the form of iris diaphragms, for changing the beam In a neodymium:YAG laser device, especially for ophthalmologic treatment according to DE 33 39 369, a focal optical systems formed of negative and positive lenses which are displaceable relative to one another are provided for enlarging or reducing the beam cross section.

OBJECT AND SUMMARY OF THE INVENTION

Accordingly, it is the primary object of the invention to provide a process and an arrangement for changing the cross section of a therapy beam, especially for irradiation of diseased areas in the eye, which makes it possible to adapt not only the size of the cross-sectional surface of the beam, but also its shape, to the peculiarities of the region of the eye to be irradiated in an optimum manner and accordingly to achieve a careful treatment of the eye. In particular, this type of adaptation is desirable in photodynamic therapy of the ocular fundus and for treating age-related macular degeneration in order to protect healthy areas from the radiation.

According to the invention, this object is met in a process for changing the cross section of a therapy beam, in accordance with the invention, for targeted application of therapy radiation in the treatment of diseased areas in the eye by means of a therapy beam which is directed into the eye through an applicator. The process comprises the steps of producing an image of the fundus of the eye to be treated for determining the parameters characterizing the diseased area, deriving parameters characterizing the shape and/or size of the area to be irradiated and controlling variables from this fundus image and further processing them by a computer, controlling a control device by these parameters and controlling variables, adjusting or displacing an actuating arrangement by the control device corresponding to the shape and/or size of the area to be irradiated, and changing the shape and/or size of the cross section or changing the direction of the therapy laser beam by the actuating arrangement in a plurality of coordinates. The actuating arrangement is arranged in the beam path of the therapy beam.

Additional configurations of the inventive process and an arrangement for carrying out the process are also described.

In one embodiment of the process, the fundus of the eye to be irradiated is imaged on a CCD matrix of a CCD camera. The information is read out of the camera by a computer and further processed to obtain parameters of the region to be irradiated which characterize the shape and magnitude. Controlling variables are derived from these parameters and control an actuating arrangement arranged in the therapy beam path such that the cross section of the therapy spot at the treated area extensively corresponds to the size and shape of the diseased area in the eye.

It can also be considered as advantageous with respect to manual adjustment or adaptation of the therapy beam cross section when a fundus image of the eye to be treated is produced by means of a camera and when, on the basis of this image, the treating physician adjusts a diaphragm arranged in the beam path of the therapy beam for extensively adapting the shape and/or size of the cross section of the therapy beam passing the diaphragm to the diseased area of the eye to be irradiated.

In another advantageous modification of the process for targeted application of the therapy beam in the interior of the eye for meeting the object stated above, the fundus of the eye (e.g., the retina) is line-scanned by a target beam (separate laser source or reduced-output therapy beam source). The target beam and therapy beam traverse the same adjusting device and are consequently adapted to one another with respect to placement, size and shape. The respective position of this scanning target beam on the fundus of the eye is determined by a computer either directly from information of the CCD camera or indirectly from the actuating information of the utilized beam deflecting unit. When the position of the scanning beam is determined indirectly, signals relevant to position are obtained from the position of the deflecting elements of the beam deflecting unit by means of angle sensors and path measurement sensors and are further processed by a computer for determining the position of the target beam and therapy beam in the CCD image. If the position of the target beam lies within the area to be irradiated, the therapy beam is applied with the power needed for irradiation. When the target beam leaves the area to be irradiated, the output of the therapy beam is reduced again below the level needed for treatment.

An arrangement for targeted application of a therapy beam for irradiation of diseased areas in the interior of the eye comprises at least one radiation source for generating the therapy beam and/or a target beam, an applicator for directing the therapy beam into the eye to be treated, wherein the applicator is optically connected with the radiation sources, imaging optical elements, and an actuating arrangement for changing the shape and size of the beam cross section of the therapy beam or its direction. Further, means are provided for producing a fundus image and means are provided for obtaining shape parameters and size parameters from the area to be irradiated. These parameters are fed to a computer for processing and controlling the therapy beam with respect to output, emission duration and direction.

The actuating arrangement for changing the shape and/or size of the cross section of the therapy beam is advantageously arranged in an intermediate image plane of the therapy beam path of the applicator. A controllable diaphragm arrangement or closure arrangement by means of which the therapy beam is adapted can also be arranged in the intermediate image plane of the therapy beam path.

It is also advantageous when the actuating arrangement is a controllable LCD matrix which is arranged in the beam path in the intermediate image plane of the applicator and which is controlled by the computer in such a way that after the therapy beam has traversed the LCD arrangement or been reflected by it the cross section of the therapy beam extensively corresponds in shape and size to the surface of the diseased area of the eye to be treated.

According to an advantageous development of the arrangement according to the invention, a scanning or deflecting device which is controlled by the computer corresponding to the above-mentioned parameters is provided in the beam path of the applicator as an actuating arrangement and directs the therapy beam in a targeted manner on the area of the fundus' to be irradiated. A scanning or deflecting device of this kind has, for example, at least one reflector which is tiltable about two axes or another beam-deflecting optical element whose position is controllable in a targeted manner depending on the above-mentioned parameters. This scanning or deflecting device is advantageously outfitted with measurement systems with which the position, e.g., of the reflector is indicated or by means of which signals characterizing the position of these reflectors are generated, which signals are then fed to the computer and further processed thereby for purposes of controlling the therapy beam.

A diaphragm with an adjustable aperture and a cover element which covers this aperture at least partially can also be provided in the intermediate image plane of the beam path of the applicator for rough adaptation of the cross section of the therapy beam to the area to be irradiated, wherein the cover element and diaphragm can be positioned relative to one another in two coordinates.

The invention will be explained more fully in the following with reference to an embodiment example.

DESCRIPTION OF THE PREFERRED EMBODIMENTS

Figure 1:
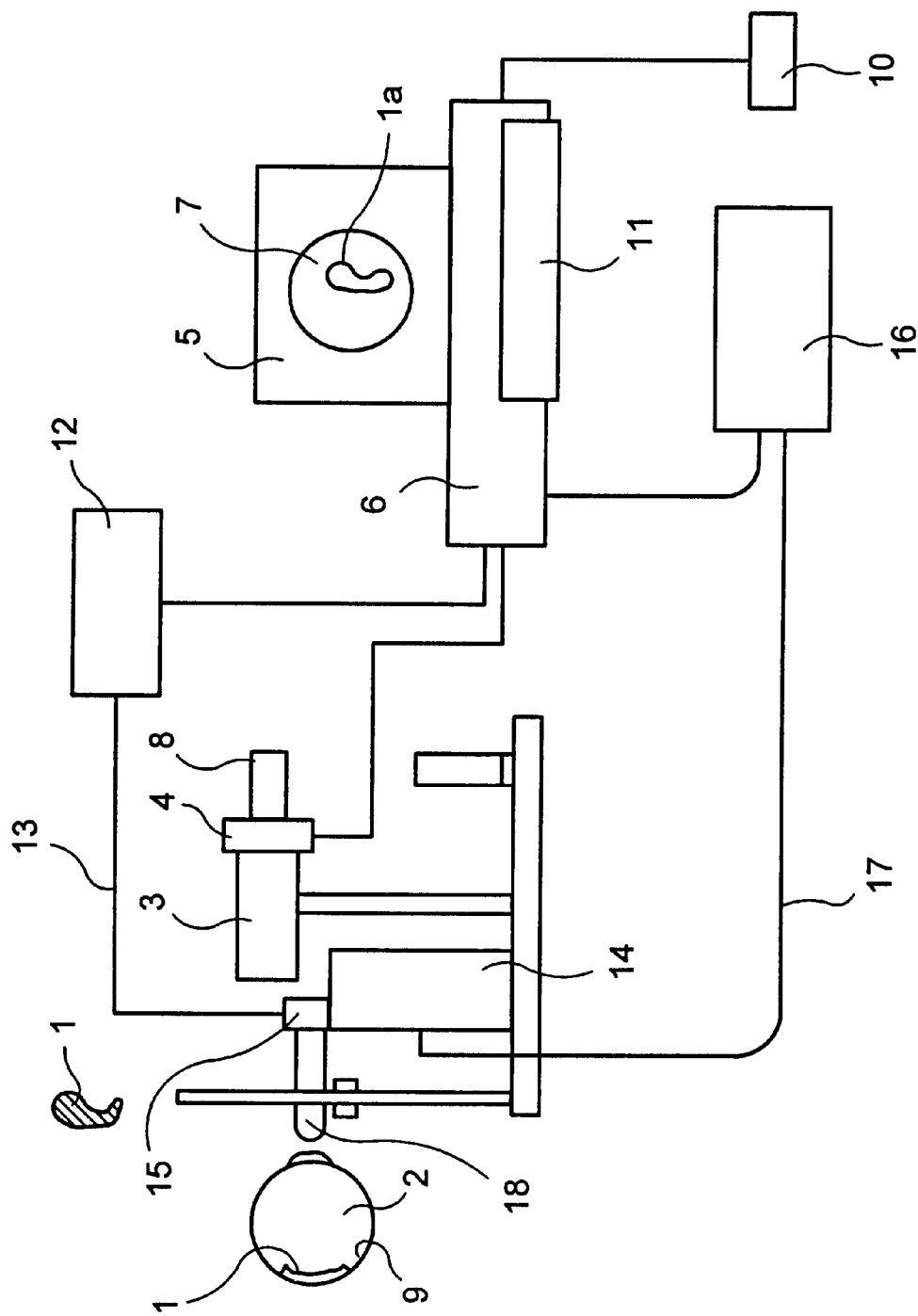
FIG. 1 shows an arrangement for carrying out the process according to the invention, shown schematically.

The process for targeted application of therapy radiation in the treatment of diseased areas 1 in the eye 2 of the patient will be described with reference to the arrangement shown schematically in FIG. 1. In order to determine parameters, target data and reference data characterizing the diseased area 1 to be treated in the eye 2, a magnified image 7 of the fundus or retina is generated by means of a microscope 3 and a camera 4 together with the image 1a of the diseased area 1 and, e.g., is displayed on a monitor 5 which is connected with a computer 6. The position, shape and size of the diseased area 1 are detected from this image 7 of the fundus. An eyepiece 8 for visual observation of the fundus or retina 9 is provided at the microscope 3. Manipulations can be carried out and data characterizing the size, position and shape of the diseased area 1 can be predetermined and entered in the computer 6 via input elements 10 and 11. These data are stored as reference data and target data and serve as a basis for the treatment. With the help of these parameters and controlling variables, reference data or target data, a control device 12, for example, which is connected by a control line 13 to an actuating arrangement 15 provided at the applicator 14 is controlled by the computer 6, wherein the cross section of the therapy beam 18 generated by a laser 16 serving as a light source is extensively adapted to the area 1 to be treated in the eye 2 of the patient with respect to shape, size and position by means of the actuating arrangement 15 and is superimposed permanently online. The laser 16 and the applicator 14 are connected with one another by a light guide 17 transmitting light. The therapy beam 18 which is adapted in shape and size to the area 1 to be treated is then directed into the eye 2 via optical elements, known per se, in the applicator 14 (not shown in FIG. 1).

Figure 2:
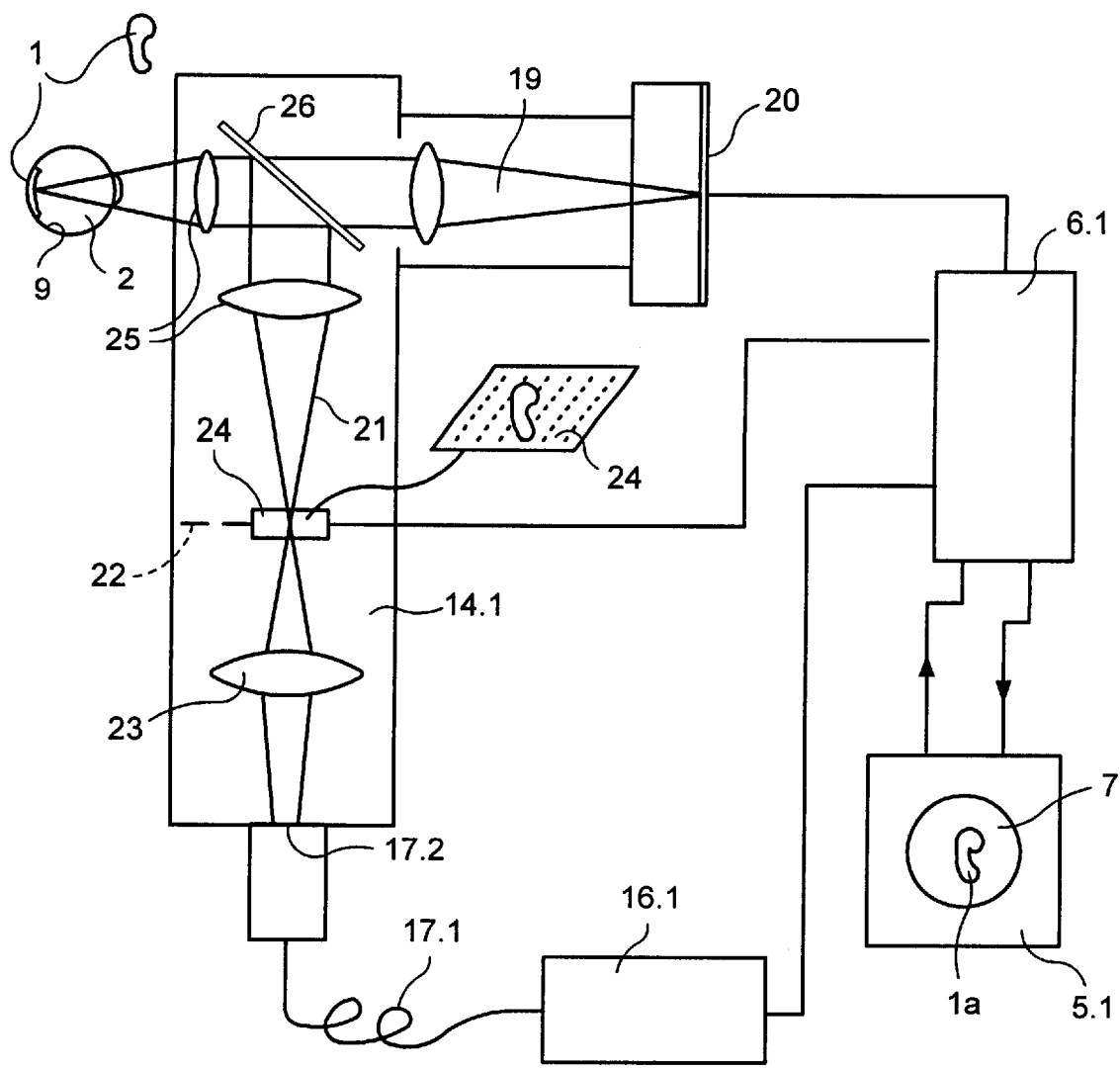
FIG. 2 shows the construction of an arrangement with CCD camera for carrying out the process according to the invention, shown schematically.

The arrangement for carrying out the process which is shown in a simplified manner in FIG. 2 likewise comprises a laser 16.1 as radiation source, an applicator 14.1 and a CCD camera 19 with a CCD matrix 20 on which the fundus or retina 9 of the eye 2 is imaged together with the area 1 to be irradiated. The signals supplied by the CCD elements of the matrix 20 are stored in the computer 6.1. The image 1a of the fundus or retina 9 can be made visible on a monitor 5.1 which is connected with the computer 6.1. The applicator 14.1 is connected with the laser 16.1 by means of a light guide 17.1 by means of which laser light is supplied to the applicator 14.1 to form the therapy beam 21. Imaging optics 25 are provided in the applicator 14.1 for imaging the light guide output 17.2 in an intermediate image plane 22. An LCD matrix 24 is provided in the intermediate image plane 22 which can be imaged on the retina 9 by additional imaging optics 25 and via a deflecting element 26, wherein the LCD elements of the LCD matrix 24 are controllable by means of corresponding signals of the computer 6.1 such that their transmittance is changed in such a way that the therapy beam 21 which has passed the matrix 24 has a cross section 24.1 which extensively corresponds in shape and size to the irradiated area 1 in the eye 2.

The LCD matrix 24 is accordingly a kind of electronically adjustable mask which is influenced by the computer 6.1 in such a way that the therapy beam corresponds in size and cross section to the reference data and to the reference shape of the beam. Throughout the entire radiation period the computer 6.1 correlates the current fundus images with the reference image (image 1a) and, as necessary, controls the LCD elements of the LCD matrix 24 in such a way that the beam profile coincides at all times with the actual diseased area.

Instead of the LCD matrix 24 shown in FIG. 2, an adjustable diaphragm arrangement comprising, e.g., an iris diaphragm or cat's eye diaphragm and a displaceable cover element can also be provided, wherein the adjustment of the size of the aperture of the diaphragm arrangement and the displacement of the cover element relative to the diaphragm aperture can be carried out by computer or manually based on patient-related and/or device-related parameters.

Figure 3:
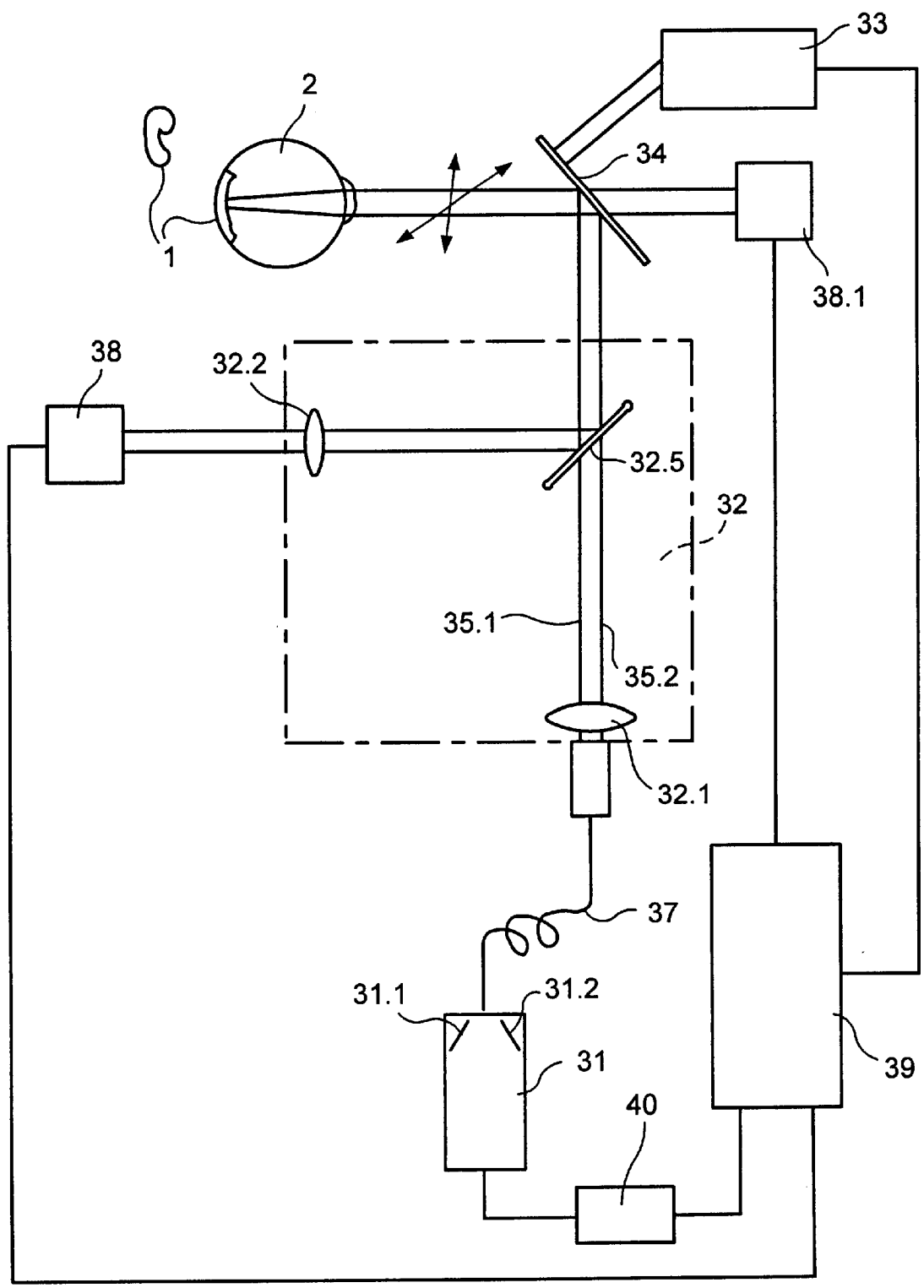
FIG. 3 shows simplified view of an arrangement with scanning beam and attenuated therapy beam.

FIG. 3 shows by way of example a simplified view of an arrangement with a target beam or a target beam serving as an attenuated therapy beam. In this arrangement, a laser 31 is provided for generating a target beam 31.1 or an attenuated therapy beam 31.2 which can also serve as a target beam. The light from the laser (31.1 and/or 31.2) is transmitted to an imaging unit 32 via a light guide 37. This imaging unit 32 includes imaging optics 32.1 and 32.2, a beam splitter 32.5 and a deflecting unit 34, e.g., in the form of a mirror, which is movable by means of a deflecting device 33 which is controllable by a computer 39. The target beam 35.1 and therapy beam 35.2 are deflected by these elements on the area 1 to be treated in the eye 2 of the patient. The arrangement according to FIG. 3 can be operated in the following ways:

a) The target beam 35.1 supplied by the laser 31, preferably via the light guide 37 of the imaging unit 32, is deflected into the eye 2 by the controlled deflecting unit 34, e.g., a reflector which is swivelable in all directions, and scans the retina. The light of the target beam 35.1 reflected by the retina of the eye 2 is then guided via the scanning unit 34 and beam splitter 32.5 to a location-sensitive receiver arrangement 38, for example, a CCD matrix, which is connected with the computer 39. Alternatively, the receiver arrangement can also be arranged as a CCD matrix 38.1 behind the deflecting mirror 34 for observing the findus 1 of the diseased eye 2. The deflecting mirror 34 must consequently enable geometric or dichroic beam splitting. A control unit 40 for the laser 31 is controlled by signals supplied by the computer 39 in such a way that a therapy beam 35.2 is generated or released for application during the scanning of the diseased area 1 to be treated in the eye 2 by the target beam 35.1. However, if the target beam 35.1 passes over healthy areas of the retina during the scanning, the generation or release of a therapy beam is interrupted.

b) In this mode of operation, the fundus of the eye or the retina is not scanned by a separate target beam, but rather by a therapy beam 35.2 of diminished intensity. The light reflected by the retina or fundus of the eye is directed to the receiver arrangement 38 or 38.1. The signals supplied by the computer 39 are also used in this case to control the control unit 40 in such a way that the therapy beam 35.2 is switched to the intensity necessary for irradiation whenever the beam scans the diseased area 1 in the eye. When the scanning beam passes over healthy areas of the retina, it is switched back to an attenuated therapy beam.

Intravenous contrast agents or fluorescent dyes or medications may be used and suitably excited to obtain the fundus image and serve to improve contrast or clarify the disease and can also serve for treating the diseased area.

While the foregoing description and drawings represent the preferred embodiments of the present invention, it will be obvious to those skilled in the art that various changes and modifications may be made therein without departing from the true spirit and scope of the present invention.

What is claimed is:

1. A process for targeted application of therapy radiation in the treatment of diseased areas in the eye by means of a therapy beam which is directed into the eye through an applicator, comprising the steps of:

producing an image of the fundus of the eye to be treated for determining parameters characterizing the diseased area;

deriving parameters characterizing the shape and/or size of the area to be irradiated and controlling variables from this fundus image and further processing them by a computer;

controlling a control device by said parameters and controlling variables;

adjusting or displacing an actuating arrangement by said control device corresponding to the shape and/or size of the area to be irradiated; and changing the shape and/or size of the cross section or changing the direction of the therapy laser beam by said actuating arrangement in a plurality of coordinates, the actuating arrangement being arranged in the beam path of the therapy beam.

2. The process according to claim 1, wherein the fundus image of the eye to be irradiated is obtained through a CCD matrix.

3. The process according to claim 1, wherein the fundus image of the eye to be irradiated is obtained through a television camera.

4. The process according to claim 1, wherein intravenous contrast agents or fluorescent dyes or medications are used and suitably excited to obtain the fundus image and serve to improve contrast or clarify the disease and can also serve for treating the diseased area.

5. The process according to claim 1, wherein data are prepared in electronic or graphic form by the computer and assist in the preparation of mechanical masks or diaphragms, and wherein these data are used for controlling corresponding devices for preparing said masks.

6. The process according to claim 1, wherein suggestions concerning the shape and size of the diseased surface are made independently by the computer or a selection of the area to be treated is carried out by the computer.

7. A process for targeted application of therapy radiation in the treatment of diseased areas in the eye by means of a therapy beam which is directed into the eye through an applicator, comprising the steps of:

producing an image of the fundus of the eye to be treated by means of a camera; and adapting, based on this image by means of manual adjustment of a diaphragm arranged in the beam path of the therapy beam, the cross section of the therapy beam passing the diaphragm in shape or size to the diseased area to be irradiated in the eye.

8. The process according to claim 1 or 7, wherein mechanical masks or diaphragms of different shapes and sizes are provided and are administered by means of an applicator controlled by a computer, and wherein a diaphragm which is suitable for therapy is introduced in the beam path of the applicator by means of actuating elements or manually.

9. The process according to claim 7, wherein data are prepared in electronic or graphic form by a computer and assist in the preparation of mechanical masks or diaphragms, and wherein these data are used for controlling corresponding devices for preparing said masks.

10. The process according to claim 7, wherein suggestions concerning the shape and size of the diseased surface are made independently by a computer or a selection of the area to be treated is carried out by a computer.

11. A process for targeted application of therapy radiation for treatment of diseased areas in the eye by means of a therapy beam which is directed into the eye through an applicator, comprising the steps of:

line-scanning of the ocular findus (retina) with a target beam or with a reduced-output therapy beam, wherein the target beam or reduced therapy beam is deflected by a beam deflecting unit acting in two coordinates; and determining the respective position of the scanning target beam or reduced therapy beam on the ocular fundus by means of a computer such that the output necessary for irradiation is applied to a therapy beam during the scanning of a scanning beam within the area to be irradiated or within an image of this area.

12. The process according to claim 11, wherein the position of a target beam is determined from the fundus image through suitable image processing methods based on characterizing quantities by means of a computer.

13. The process according to claim 11, wherein the position of the scanning target beam or reduced therapy beam is determined by the computer from the measured values of measurement systems proportional to the respective angular position of the beam deflecting unit.

14. An arrangement for targeted application of a therapy beam in a device for irradiation of diseased areas in the interior of the eye, the arrangement comprising:

at least one light source for generating a therapy beam and/or a target beam;

an applicator for directing the target beam and/or therapy beam into the eye to be treated, wherein the applicator is optically connected with the at least one light source;

imaging optics located in the applicator;

an actuating arrangement for changing the shape and size of the beam cross section of the target beam and/or therapy beam or a beam deflecting unit for changing the direction of the target beam and/or therapy beam;

means for producing a fundus image;

means for obtaining parameters characterizing the shape and/or size of the area to be irradiated in the eye; and a computer for processing the parameters and controlling the therapy beam with respect to output, emission duration and direction.

15. The arrangement according to claim 14, wherein the actuating arrangement for changing the shape and/or size of the cross section or direction of the therapy beam is arranged in an intermediate image plane of the therapy beam path of the applicator.

16. The arrangement according to claim 14, wherein a controllable diaphragm arrangement or closure arrangement is arranged in the intermediate image plane of the therapy beam path.

17. The arrangement according to claim 14, wherein a scanning or beam deflecting unit which is controlled by the computer corresponding to said parameters is provided in the beam path of the applicator and directs the therapy beam in a targeted and permanently automatic manner on the area of the eye to be irradiated.

18. The arrangement according to claim 14, wherein the actuating arrangement is formed of a diaphragm with adjustable aperture and a cover element which covers this aperture at least partially, wherein the cover element and diaphragm can be positioned relative to one another with respect to angle in two coordinates.

* * * * *